United States Patent [19]
Schmidt et al.

[11] Patent Number: 5,565,617
[45] Date of Patent: Oct. 15, 1996

[54] PROCESS FOR PURIFYING AN ALKYLATE STREAM

[75] Inventors: Robert J. Schmidt, Barrington; Paul A. Sechrist, Des Plaines; Paul T. Barger, Arlington Heights; Christopher D. Gosling, Roselle, all of Ill.

[73] Assignee: UOP, Des Plaines, Ill.

[21] Appl. No.: 445,619

[22] Filed: May 22, 1995

[51] Int. Cl.⁶ ........................................ C07C 7/00
[52] U.S. Cl. ................ 585/802; 585/800; 585/841; 585/833; 585/734; 585/738; 585/719; 585/712
[58] Field of Search ................................ 585/800, 802, 585/841, 833, 734, 738, 719, 712

[56] References Cited

U.S. PATENT DOCUMENTS

| | | | |
|---|---|---|---|
| 3,751,489 | 8/1973 | Sobel | 585/719 |
| 4,105,707 | 8/1978 | Little et al. | 260/683.48 |

*Primary Examiner*—Asok Pal
*Assistant Examiner*—In Suk Bullock
*Attorney, Agent, or Firm*—Thomas K. McBride; Eugene I. Snyder; Frank S. Molinaro

[57] ABSTRACT

A process for purifying an alkylate feedstream is disclosed. The feedstream contains hydrogen, hydrogen chloride, $C_2$–$C_{7+}$ alkanes, $C_2$–$C_6$ alkenes and $C_2$–$C_6$ alkyl halides. The process involves flowing the alkylate through a series of separation zones and a reaction zone to provide a halide free alkylate stream.

8 Claims, 1 Drawing Sheet

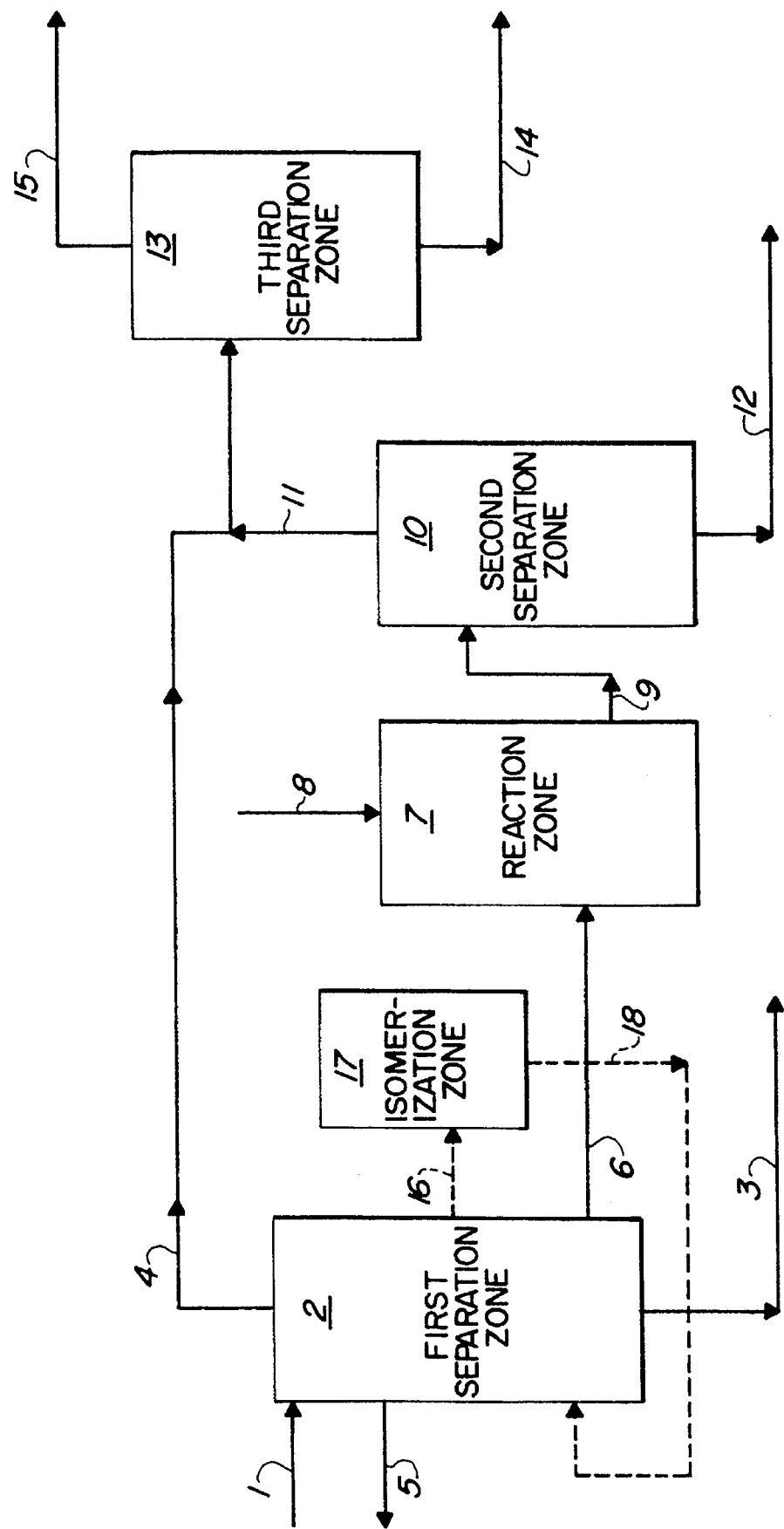

5,565,617

PROCESS FOR PURIFYING AN ALKYLATE STREAM

FIELD OF THE INVENTION

This invention relates to a process for purifying an alkylate feedstream containing alkyl halides and hydrogen halide impurities. The process involves flowing the alkylate feedstream through a series of reactors to provide a chloride free alkylate stream.

BACKGROUND OF THE INVENTION

One major component of motor fuel is "alkylate". "Alkylate" generally refers to a mixture of alkanes resulting from the alkylation of $C_2$–$C_6$ olefins (alkenes) by $C_4$–$C_6$ alkanes. It is desirable that the product mixture, i.e. alkylate, contains predominantly trimethylpentanes since these are high octane components which add considerable value to motor fuel. The use of alkylate as a motor fuel component has become more important owing to government regulations on lead and butane. In the past, adding lead anti-knock compounds was the easiest way to increase gasoline octane, but because of the deleterious effects of lead emissions the Environmental Protection Agency (EPA) has mandated the phasing out of lead in gasoline. Butane is another effective octane booster but easily evaporates, especially in warm weather, contributing to smog formation. The EPA has also required the reduction of butane from gasoline.

The alkylation of olefins by alkanes to give alkylate is a well known reaction and is generally catalyzed by strong acids. Sulfuric acid and liquid HF are the commercial catalysts of choice because of their high conversion and selectivity. Of these two catalysts, HF has been favored partly because of the relative ease of HF regeneration.

Recently hydrofluoric acid (HF) has come under environmental scrutiny owing to its classification as an Acutely Hazardous Material. Further, in Southern California the Board of the South Coast Air Quality Management District recently required that the use of HF in alkylation be phased out by Jan. 1, 1998. Accordingly, there are incentives for finding substitutes for HF. One such substitute is a solid catalyst which is the reaction product between one or more of the metal halides active as Friedel-Crafts catalysts and a refractory inorganic oxide having surface hydroxyl groups. The refractory inorganic oxide also has dispersed on it a metal having hydrogenation activity for olefins.

One problem associated with solid bed catalysts is that they have limited stability with lifetimes under 6 hours being common. Attempts at solving this problem have centered on using halides in the feedstream. One such procedure involves using hydrogen halides and/or alkyl halides as the halogen source. However, this results in halogen being present in the product alkylate stream. Accordingly, applicants have developed a process which effectively removes halides from the product stream and recycles these components in order to optimize the process.

SUMMARY OF THE INVENTION

As stated, this invention relates to a process for purifying an alkylate feedstream containing alkyl halides and hydrogen halide. Accordingly, one embodiment of the invention is a process for purifying an alkylate feedstream comprising $C_2$–$C_{7+}$ alkanes, $C_2$–$C_6$ alkenes, $C_2$–$C_6$ alkyl halides and hydrogen chloride, the process comprising flowing the feedstream into a first separation zone operated at conditions to separate said feedstream into a first overhead stream containing hydrogen, hydrogen chloride, propane and isobutane, a first side stream containing isobutane and hydrogen chloride, a second side stream containing $C_5$/$C_6$ alkanes and alkyl halides and a bottom stream containing $C_{7+}$ alkanes; flowing the second side stream to a reaction zone and contacting the second side stream with a catalyst and hydrogen at reaction conditions, thereby converting the alkyl halides to alkanes and hydrogen chloride, flowing the product effluent from the reaction zone to a second separation zone operated at conditions to separate the product effluent into a second bottom stream containing $C_5$/$C_6$ alkanes and a second overhead stream containing hydrogen, hydrogen chloride and butanes. Optionally, the second overhead stream can be combined with the first overhead stream and the combined stream flowed into a third separation zone operated at conditions to provide a third overhead stream containing propane and hydrogen chloride and a third bottom stream containing isobutane.

BRIEF DESCRIPTION OF THE DRAWING

The Drawing is a simplified process flow diagram of one embodiment of the invention showing the purification of an alkylate feedstream.

DETAILED DESCRIPTION OF THE INVENTION

As stated, the instant invention relates to a process for purifying an alkylate feedstream. Although the actual reaction to produce the alkylate feedstream is not an essential part of this invention, a brief description is presented for completeness.

The alkylate feedstream is produced in an alkylation zone where an alkane is reacted with an olefin in the presence of a hydrogen halide or alkyl halide using a solid acid catalyst. The alkanes which are used are those that contain from 4 to 6 carbon atoms with branched alkanes being preferred, e.g., isobutane. The olefins which are used are those that have from 3–6 carbon atoms and preferably 4–5 carbon atoms, e.g., 1-butene, isobutylene, 2-butenes, etc. The alkyl halides are those having from 3 to about 5 carbon atoms. The chlorides and bromides are preferred alkyl halides with the alkyl chlorides being most preferred, e.g., 1-chlorobutane, 2-chlorobutane, tert-butyl chloride, etc. In the description which follows, chloride and alkyl chloride will be used to exemplify halides, but this should not be taken as limiting the invention to chloride.

The reaction between alkanes and olefins or alkyl chlorides to form alkylate is catalyzed by solid acid catalysts. Generally effective catalysts are solid acid catalysts identified as strong Lewis acids as well as supported sulfuric and phosphoric acids. Examples of such materials include silica impregnated with sulfuric acid (U.S. Pat. No. 5,336,833), heteropoly acids, as exemplified by heteropolymolybdates and heteropolytungstates, especially as supported on molecular sieves (see, U.S. Pat. No. 5,324,881 for examples of heteropoly acids as well as supports), sulfated zirconia as exemplified in U.S. Pat. No. 5,310,868, various zeolitic materials as summarized in U.S. Pat. No. 5,258,569, supported fluorinated sulfonic acids (U.S. Pat. No. 5,245,100), Lewis acids such as $BF_3$, $SbF_5$, $AlCl_3$, $GaCl_3$, and so forth (U.S. Pat. No. 5,245,101; 5,190,904; 5,157,197) either alone or in combination with zeolitic materials (U.S. Pat. No. 5,191,148) or as composites. The Lewis acids based on aluminum, gallium, antimony and boron halides are especially attractive. All said above references are incorporated by reference.

The reaction conditions for effecting alkylation clearly will depend upon the alkane, olefin and alkyl chloride used as well as the particular catalyst employed. Sufficient pressure is used to ensure a liquid phase reaction, but the pressure is otherwise unimportant as a reaction variable influencing the course of alkylation. Clearly the pressure necessary to maintain a liquid phase reaction depends upon the reaction temperature as well as the reactant, but pressures in the range of 100–1500 psig generally will suffice. Alkylation temperatures may be as low as about −40° C. and as high as about 150° C., depending upon the reactants as well as the particular solid acid catalyst used. For example, for the preferred catalyst described above temperatures between about 0° C. and about 50° C. generally will suffice and are preferred.

The alkylation reaction is carried out in an alkylation zone as a continuous reaction with the reactants in the liquid phase. The catalytic composite is present either as a fixed bed or a moving bed and the reaction stream containing a mixture of alkyl chlorides, olefins and alkanes is flowed either in an upflow or downflow mode over the catalyst. The feedstock generally is flowed over the catalyst at a liquid hourly space velocity of about 0.5 to about 5.0 $hr^{-1}$.

Regardless of how the alkylation is carried out, the product stream from the alkylation zone will contain a mixture of components including hydrogen halides, hydrogen, isobutane, $C_2$–$C_{7+}$ alkanes, $C_4$–$C_6$ alkenes, alkyl halides and trace levels of cyclic compounds. This product stream, which will be referred to as the alkylate feedstream is now flowed to a first separation zone which is operated at conditions necessary to separate the feedstream into a first overhead stream, a first side stream, a second side stream and a bottom stream. The first overhead stream comprises mainly hydrogen and hydrogen chloride with small amounts of propane and isobutane. The first side stream comprises mainly isobutane with minor amounts of hydrogen chloride and n-butane, while the second side stream contains $C_5$/$C_6$ alkanes as the main component with some n-butane and minor amounts of alkyl halides. Finally, the bottom stream contains $C_{7+}$ alkanes. The conditions in this first separation zone include a temperature of about 35° C. to about 240° C. and a pressure of about 689 kPa (100 psig) to about 1724 kPa (250 psig). The bottom stream containing $C_{7+}$ alkanes is collected and blended with other hydrocarbons to give a motor fuel product while the first side stream is recycled to the alkylation zone.

The second side stream containing alkanes and alkyl halides is now flowed to a reaction zone where the alkyl halides are reacted with hydrogen in the presence of a catalyst to give alkanes and hydrogen chloride. The catalyst which is used to catalyze this reaction is the solid acid catalyst used in the alkylation zone described above. Particularly it is the spent catalyst from the alkylation zone. Thus, the solid acid catalyst is used to catalyze the reaction of hydrogen with alkyl halides. Simultaneously, the reaction mixture regenerates the alkylation catalyst. The conditions which are used in this reaction zone include a temperature of about 90° C. to about 250° C., a pressure of about 689 kPa (100 psig) to about 4826 kPa (700 psig) and a minimum particle Reynolds Number of about 10.

The product effluent from the reaction zone is flowed to a second separation zone operated at conditions to separate the product effluent into a second bottom stream containing $C_5$/$C_6$ alkanes and a second overhead stream containing hydrogen, hydrogen chloride and butanes. This second separation zone is operated at a temperature of about 35° C. to about 110° C. and a pressure of about 689 kPa (100 psig) to about 1724 kPa (250 psig). The bottom stream is collected and blended with motor fuel or heavy alkylate from the bottoms stream from the first separation zone.

The second overhead stream is now combined with the first overhead stream and the combined stream is flowed into an optional third separation zone operated at conditions to separate the combined stream into a third overhead stream containing propane hydrogen and hydrogen chloride and a third bottom stream containing isobutane. The third bottom stream can be recycled to the alkylation zone. The operating conditions of this third separation zone include a temperature of about 30° C. to about 65° C. and a pressure of about 1034 kPa (150 psig) to about 1724 kPa (250 psig).

As another option, the first separation zone can be operated in a manner such that a third side stream containing n-butane is withdrawn and flowed into an isomerization zone where the n-butane is isomerized to isobutane by contacting the n-butane with an isomerization catalyst at isomerization conditions. Isomerization catalysts and conditions are well known in the art and are described in U.S. Pat. Nos. 2,999,074; 3,652,697; 3,128,319 and 3,112,351, all of which are incorporated by reference. The catalyst generally is one in which a metal halide of the Friedel-Crafts type is reacted with a refractory metal oxide and said support also has dispersed thereon a platinum group metal. The isomerization conditions include a temperature of about 0° C. to about 500° C. and a pressure of about 101 kPa (14.7 psi) to about 20,265 kPa (2940 psi). The effluent from this isomerization zone is recycled into the first separation zone in order to separate the isobutane from unreacted n-butane.

The Drawing illustrates one embodiment of the invention. Those skilled in the art will recognize that this process flow diagram has been simplified by the elimination of many pieces of process equipment including heat exchangers, process control systems, pumps, fractionation column overhead and reboiler systems, etc. which are not necessary to an understanding of the process. It may also be readily discerned that the process flow presented in the drawings may be modified in many aspects without departing from the basic overall concept of the invention. Referring now to the Drawing, an alkylate feedstream comprising $C_{2-7+}$ alkanes, $C_2$–$C_6$ alkenes, $C_2$–$C_6$ alkyl halides, hydrogen and hydrogen chloride is flowed via line 1 into a first separation zone 2 operated at conditions in order to separate the feedstream into a first overhead stream containing hydrogen, hydrogen chloride, with small amounts of propane and isobutane which is removed via line 4, a first side stream containing isobutane, hydrogen, chloride and n-butane which is removed via line 5, a second side stream containing $C_5$/$C_6$ alkanes and alkyl halides is removed via line 6 and a bottom stream containing $C_{7+}$ alkanes is removed via line 3 and collected. The first side stream which is removed via line 5 is recycled to the alkylation zone (not shown).

Next, the second side stream is flowed via line 6 into reaction zone 7 where the alkyl halides in said stream are reacted with hydrogen which is flowed into reaction zone 7 via line 8. The reaction of alkyl halides with hydrogen is catalyzed by a spent solid alkylation catalyst which is simultaneously regenerated by the reaction mixture. The product effluent from reaction zone 7 is removed via line 9 into a second separation zone 10 operated at conditions to separate the product effluent into a second bottom stream containing $C_5$/$C_6$ alkanes which is removed via line 12 and a second overhead stream containing hydrogen, hydrogen chloride and butanes which is removed via line 11.

The second overhead stream which is removed via line 11 is combined with the first overhead stream via line 4. This combined stream can be either further processed to remove hydrogen chloride from the stream (not shown) or it can be flowed into a third separation zone 13 operated at conditions to separate the combined stream into a third overhead stream containing propane and hydrogen chloride which is removed via line 15 and a third bottom stream containing isobutane which is removed via line 14. The third overhead stream can be further processed to separate the propane from the hydrogen chloride (not shown). Finally, the isobutane in the third bottom stream can be recycled to the alkylation zone.

The first separation zone 1 can optionally be operated in a manner to separate a third side stream containing n-butane which is removed via line 16. The third side stream is now flowed into isomerization zone 17 where it is contacted with an isomerization catalyst, thereby converting the n-butane to isobutane. The effluent from isomerization zone 17 which contains n-butane and isobutane, is removed via line 18 and recycled to separation zone 1 in order to separate the n-butane and isobutane.

We claim as our invention:

1. A process for purifying an alkylate feedstream comprising $C_2$–$C_{7+}$ alkanes, $C_2$–$C_6$ alkenes, $C_2$–$C_6$ alkyl chlorides and hydrogen chloride, the process comprising flowing the feedstream into a first separation zone operated at conditions to separate said feedstream into a first overhead stream containing hydrogen, hydrogen chloride, propane and isobutane, a first side stream containing isobutane and hydrogen chloride, a second side stream containing $C_5/C_6$ alkanes and alkyl chlorides and a bottom stream containing $C_{7+}$ alkanes; flowing the second side stream to a reaction zone and contacting the second side stream with a catalyst and hydrogen at reaction conditions, thereby converting the alkyl chlorides to alkanes and hydrogen chloride, flowing the product effluent from the reaction zone to a second separation zone operated at conditions to separate the product effluent into a second bottom stream containing $C_5/C_6$ alkanes and a second overhead stream containing hydrogen, hydrogen chloride and butanes.

2. The process of claim 1 further characterized in that the second overhead stream is combined with the first overhead stream, and the combined stream is flowed into a third separation zone operated at conditions to provide a third overhead stream containing propane and hydrogen chloride and a third bottom stream containing isobutane.

3. The process of claim 1 where the separation conditions in the first separation zone include a temperature of about 35° C. to about 240° C. and a pressure of about 689 kPa to about 1724 kPa.

4. The process of claim 1 where the reaction conditions include a temperature of about 90° C. to about 250° C., a pressure of about 689 kPa to about 4826 kPa and a minimum particle Reynolds Number of about 10.

5. The process of claim 1 where the separation conditions in the second separation zone include a temperature of about 35° C. to about 100° C. and a pressure of 689 kPa to about 1724 kPa.

6. The process of claim 2 where the conditions in the third separation zone include a temperature of about 30° C. to about 65° C. and a pressure of about 1034 kPa to about 1724 kPa.

7. The process of claim 1 further characterized in that a third side stream containing n-butane is separated from the first separation zone, flowed to an isomerization zone where the n-butane is contacted with an isomerization catalyst at isomerization conditions, thereby isomerizing the n-butane to isobutane and flowing the effluent from the isomerization zone to the first separation zone.

8. The process of claim 7 where the isomerization conditions include a temperature of about 0° C. to about 500° C. and a pressure of about 101 kPa to about 20,265 kPa.

* * * * *